(12) United States Patent
Kiers et al.

(10) Patent No.: US 7,692,792 B2
(45) Date of Patent: Apr. 6, 2010

(54) METHOD AND APPARATUS FOR ANGULAR-RESOLVED SPECTROSCOPIC LITHOGRAPHY CHARACTERIZATION

(75) Inventors: Antoine Gaston Marie Kiers, Veldhoven (NL); Arie Jeffrey Den Boef, Waalre (NL); Stefan Carolus Jacobus Antonius Keij, Breda (NL)

(73) Assignee: ASML Netherlands B.V., Veldhoven (NL)

(*) Notice: Subject to any disclaimer, the term of this patent is extended or adjusted under 35 U.S.C. 154(b) by 700 days.

(21) Appl. No.: 11/472,565

(22) Filed: Jun. 22, 2006

(65) Prior Publication Data
US 2007/0296973 A1    Dec. 27, 2007

(51) Int. Cl.
G01J 4/00    (2006.01)
(52) U.S. Cl. ................................ 356/369; 356/366
(58) Field of Classification Search ................ 356/366, 356/364, 369
See application file for complete search history.

(56) References Cited

U.S. PATENT DOCUMENTS

| | | | | |
|---|---|---|---|---|
| 4,723,315 | A | * | 2/1988 | Wetherell .................. 398/203 |
| 5,412,473 | A | * | 5/1995 | Rosencwaig et al. ........ 356/451 |
| 5,703,692 | A | | 12/1997 | McNeil et al. .............. 356/445 |
| 5,880,838 | A | | 3/1999 | Marx et al. ................ 356/351 |
| 5,963,329 | A | | 10/1999 | Conrad et al. .............. 356/372 |
| 6,608,690 | B2 | | 8/2003 | Niu et al. .................... 356/635 |
| 6,699,624 | B2 | | 3/2004 | Niu et al. ....................... 430/5 |
| 6,704,661 | B1 | | 3/2004 | Opsal et al. ................... 702/27 |
| 6,721,691 | B2 | | 4/2004 | Bao et al. ................... 702/189 |
| 6,738,138 | B2 | | 5/2004 | Wei ............................ 356/369 |
| 6,753,961 | B1 | | 6/2004 | Norton et al. ............... 356/364 |
| 6,768,983 | B1 | | 7/2004 | Jakatdar et al. ............... 706/46 |
| 6,772,084 | B2 | | 8/2004 | Bischoff et al. ............. 702/127 |
| 6,785,638 | B2 | | 8/2004 | Niu et al. .................... 702/189 |
| 6,813,034 | B2 | | 11/2004 | Rosencwaig et al. ........ 356/601 |
| 6,819,426 | B2 | | 11/2004 | Sezginer et al. ............. 356/401 |
| 6,856,408 | B2 | | 2/2005 | Raymond .................... 356/601 |

(Continued)

FOREIGN PATENT DOCUMENTS

DE        197 45 607 A1    4/1999

(Continued)

OTHER PUBLICATIONS

European Search Report issued for European Patent Application No. 07252355.8-2204, dated Aug. 28, 2007.

*Primary Examiner*—Roy Punnoose
(74) *Attorney, Agent, or Firm*—Sterne, Kessler, Goldstein & Fox P.L.L.C.

(57) ABSTRACT

Simultaneous measurement of two orthogonally polarized beams upon diffraction from a substrate is done to determine properties of the substrate. Linearly polarized light sources with their radiation polarized in orthogonal directions are passed via two non-polarizing beamsplitters, one rotated by 90° with respect to the other. The combined beam is then diffracted off a substrate before being passed back through a non-polarizing beamsplitter and through a phase shifter and a Wollaston prism before being measured by a CCD camera. In this way, the phase and intensities for various phase steps of the two polarized beams may thereby be measured and the polarization state of the beams may be determined. If the phase shifter is turned to zero (i.e. with no phase shifting), the grating of the substrate has its parameters measured with TE and TM polarized light simultaneously with the same detector system.

24 Claims, 9 Drawing Sheets

U.S. PATENT DOCUMENTS

| | | |
|---|---|---|
| 6,919,964 B2 | 7/2005 | Chu ........................... 356/601 |
| 6,928,628 B2 | 8/2005 | Seligson et al. ................. 716/4 |
| 6,972,852 B2 | 12/2005 | Opsal et al. .................. 356/625 |
| 6,974,962 B2 | 12/2005 | Brill et al. .................... 250/548 |
| 6,987,572 B2 | 1/2006 | Lakkapragada et al. ..... 356/601 |
| 7,046,376 B2 | 5/2006 | Sezginer ..................... 356/601 |
| 7,061,615 B1 | 6/2006 | Lowe-Webb ................ 356/401 |
| 7,061,623 B2 | 6/2006 | Davidson .................... 356/497 |
| 7,061,627 B2 | 6/2006 | Opsal et al. .................. 356/601 |
| 7,068,363 B2 | 6/2006 | Bevis et al. ............. 356/237.5 |
| 7,369,233 B2 * | 5/2008 | Nikoonahad et al. ........ 356/369 |
| 7,388,668 B2 * | 6/2008 | Potma et al. ................ 356/451 |
| 2004/0119970 A1 | 6/2004 | Dusa et al. ............... 356/237.1 |
| 2004/0227951 A1 | 11/2004 | Hill |
| 2006/0033921 A1 | 2/2006 | Den Boef et al. ........... 356/446 |
| 2006/0066855 A1 | 3/2006 | Den Boef et al. ........... 356/401 |
| 2006/0126074 A1 | 6/2006 | Van Der Werf et al. ..... 356/489 |
| 2006/0139592 A1 | 6/2006 | Den Boef et al. ............. 355/53 |
| 2008/0198380 A1 * | 8/2008 | Straaijer et al. ............. 356/369 |

FOREIGN PATENT DOCUMENTS

| | | |
|---|---|---|
| EP | 1 628 164 A2 | 2/2006 |
| EP | 1628164 A2 * | 2/2006 |
| WO | WO 01/13079 A1 | 2/2001 |

* cited by examiner

METHOD AND APPARATUS FOR ANGULAR-RESOLVED SPECTROSCOPIC LITHOGRAPHY CHARACTERIZATION

BACKGROUND OF THE INVENTION

1. Field of the Invention

The present invention relates to methods of inspection usable, for example, in the manufacture of devices by lithographic techniques and to methods of manufacturing devices using lithographic techniques, etching applications and thin-film metrology.

2. Description of the Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include steppers, in which each target portion is irradiated by exposing an entire pattern onto the target portion at one time, and scanners, in which each target portion is irradiated by scanning the pattern through a radiation beam in a given direction (the "scanning" direction) while synchronously scanning the substrate parallel or anti-parallel to this direction. It is also possible to transfer the pattern from the patterning device to the substrate by imprinting the pattern onto the substrate.

In order to determine features of the substrate, such as its layer thickness, critical dimension (CD) or overlay, a beam is reflected off the surface of the substrate, for example at an alignment target, and an image is created on a camera of the reflected beam. By measuring the properties of the reflected beam, the properties of the substrate can be determined. This can be done, for example, by comparing the reflected beam with data stored in a library of known measurements associated with known substrate properties.

One way of measuring the properties of a substrate is by diffracting a polarized beam off a grating that is present on the surface of the substrate and imaging the diffracted spectrum of the polarized beam on a detector array. The polarization state of the measurement beam must be controlled so that the polarization state is not altered by imperfections of the sensor optics. One way of doing this is shown in FIG. 2. Two sources, P and S, are merged using a polarizing beamsplitter PBS. The use of the PBS ensures that the light from the P and S sources are S and P polarized respectively (i.e. the polarization of the beams is perpendicular and parallel to the plane of incidence of the PBS respectively). In order to be able to measure the diffracted spectrum of each polarized beam on the same camera CCD, a shutter (not shown) is provided at each of the sources. The two beams p,s are alternately shuttered so that at any one moment in time, only one of the two polarizations is passing through the system. This requires a lot of quickly moving parts and the alternating between the two polarizations increases the time taken for tests carried out on the substrate, causing throughput time to be increased.

SUMMARY OF THE INVENTION

It is desirable to provide an apparatus that will shorten the time taken for both p and s polarized beams to be measured when the properties of a substrate are being determined According to an aspect of the invention, there is provided an inspection apparatus, lithographic apparatus or lithographic cell configured to measure a property of a substrate, comprising a light source configured to supply radiation with two orthogonal polarization directions; a lens configured to focus the radiation beam onto a substrate; a beamsplitter configured to separate the radiation beam once reflected from the surface of the substrate into two orthogonally polarized sub-beams; and a detector system configured to detect simultaneously an angle-resolved spectrum of both radiation beams reflected from a surface of the substrate.

According to another aspect of the invention, there is provided an inspection apparatus, lithographic apparatus or lithographic cell configured to measure a property of a substrate, comprising a light source configured to supply a radiation beam with two orthogonal polarization directions; a lens configured to focus the radiation beam onto a substrate; a detector system configured to detect the radiation beam reflected from the substrate; a first non-polarizing beamsplitter configured to receive the radiation beam from the source in a first direction and to reflect the radiation beam in a second direction onto the substrate and to receive the radiation beam reflected from the substrate in the second direction and to pass the radiation beam towards the detector system; a second non-polarizing beamsplitter rotated 90° with respect to the first non-polarizing beamsplitter and configured to receive the radiation beam passed from the first non-polarizing beamsplitter in the second direction, to transmit a portion of the radiation beam in the second direction to the detector and to reflect another portion of the radiation beam in a third direction, wherein the third direction is perpendicular to the second direction; and a third polarizing beamsplitter configured to receive the radiation beam passed from the second non-polarizing beamsplitter, to separate the radiation beam into orthogonally polarized sub-beams and to pass the sub-beams to the detector system, wherein the detector system is configured to detect simultaneously the reflection spectrum of both sub-beams.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
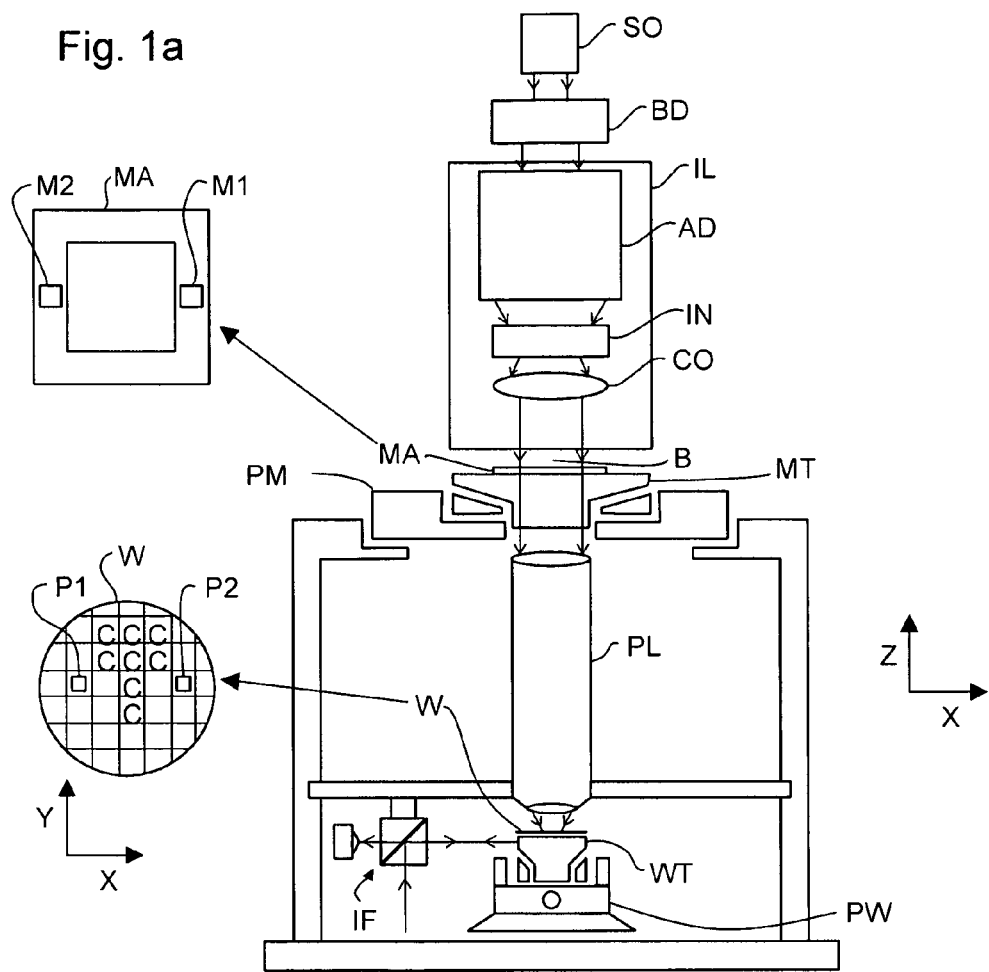
FIG. 1a depicts a lithographic apparatus according to an embodiment of the present invention.

FIG. 1a schematically depicts a lithographic apparatus. The apparatus comprises an illumination system (illuminator) IL configured to condition a radiation beam B (e.g. UV radiation or EUV radiation). A support (e.g. a mask table) MT configured to support a patterning device (e.g. a mask) MA and is connected to a first positioner PM configured to accurately position the patterning device in accordance with certain parameters. A substrate table (e.g. a wafer table) WT is configured to hold a substrate (e.g. a resist-coated wafer) W and is connected to a second positioner PW configured to accurately position the substrate in accordance with certain parameters. A projection system (e.g. a refractive projection lens system) PL is configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, to direct, shape, and/or control radiation.

The support supports, e.g. bears the weight of, the patterning device. It holds the patterning device in a manner that depends on the orientation of the patterning device, the design of the lithographic apparatus, and other conditions, such as for example whether or not the patterning device is held in a vacuum environment. The support can use mechanical, vacuum, electrostatic or other clamping techniques to hold the patterning device. The support may be a frame or a table, for example, which may be fixed or movable as required. The support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives radiation from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
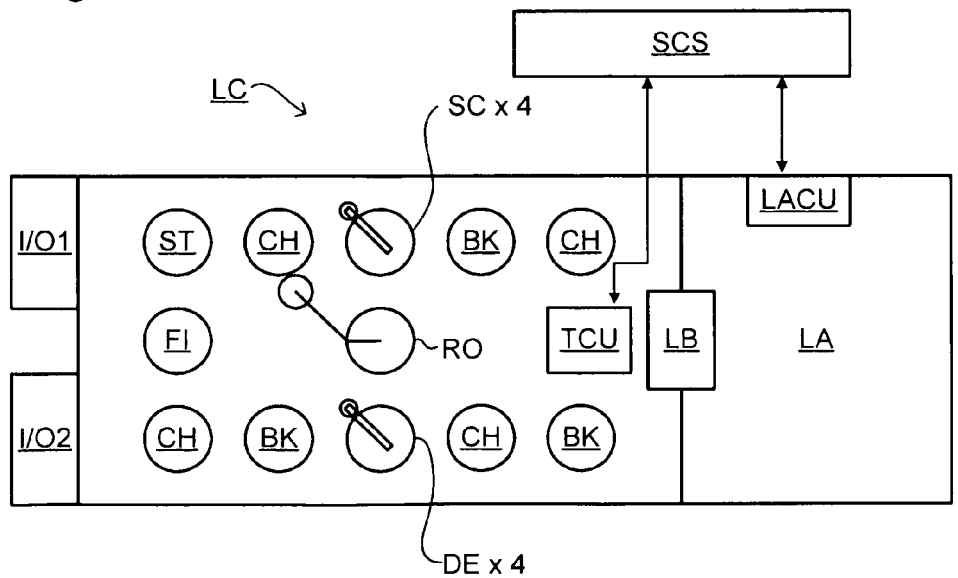
FIG. 1b depicts a lithographic cell or cluster according to an embodiment of the present invention.

As shown in FIG. 1b, the lithographic apparatus LA forms part of a lithographic cell LC, also sometimes referred to a lithocell (lithographic cell) or cluster, which also includes apparatus to perform pre- and post-exposure processes on a substrate. These include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus. Thus, the different apparatus can be operated to maximize throughput and processing efficiency.

In order that the substrates that are exposed by the lithographic apparatus are exposed consistently for each layer of resist, there are certain properties of the substrate that need to be measured to determine whether there are changes in alignment, rotation, etc., that must be compensated for by the lithographic apparatus. A separate inspection apparatus is used to determine the properties of the substrates, and in particular, how the properties of different substrates or different layers of the same substrate vary from layer to layer.

As discussed above, FIG. 2 depicts an inspection apparatus according to the state of the art. Two sources of light P, S supply radiation beams that enter a polarizing beam splitter PBS, which, although it may change the direction of the polarization, keeps the two beams orthogonally polarized, and the two beams enter a non-polarizing beam splitter NPBS before being deflected through a microscope objective 24 onto a grating 30 on substrate W. The polarized beams are diffracted by the grating 30 and are reflected upwards through the microscope objective 24, back through the non-polarizing beam splitter NPBS, through two focusing lenses L that image the back-focal plane, which is the same as the pupil plane, onto a camera CCD. The two orthogonally polarized beams are not sent through the system simultaneously. Shutters at the radiation sources P,S alternately open and close such that only polarized beam p or polarized beam s passes through the system at any single moment in time. At point 20, therefore, only one polarized beam will impinge on the camera CCD and be measured at any time t.

Figure 2:
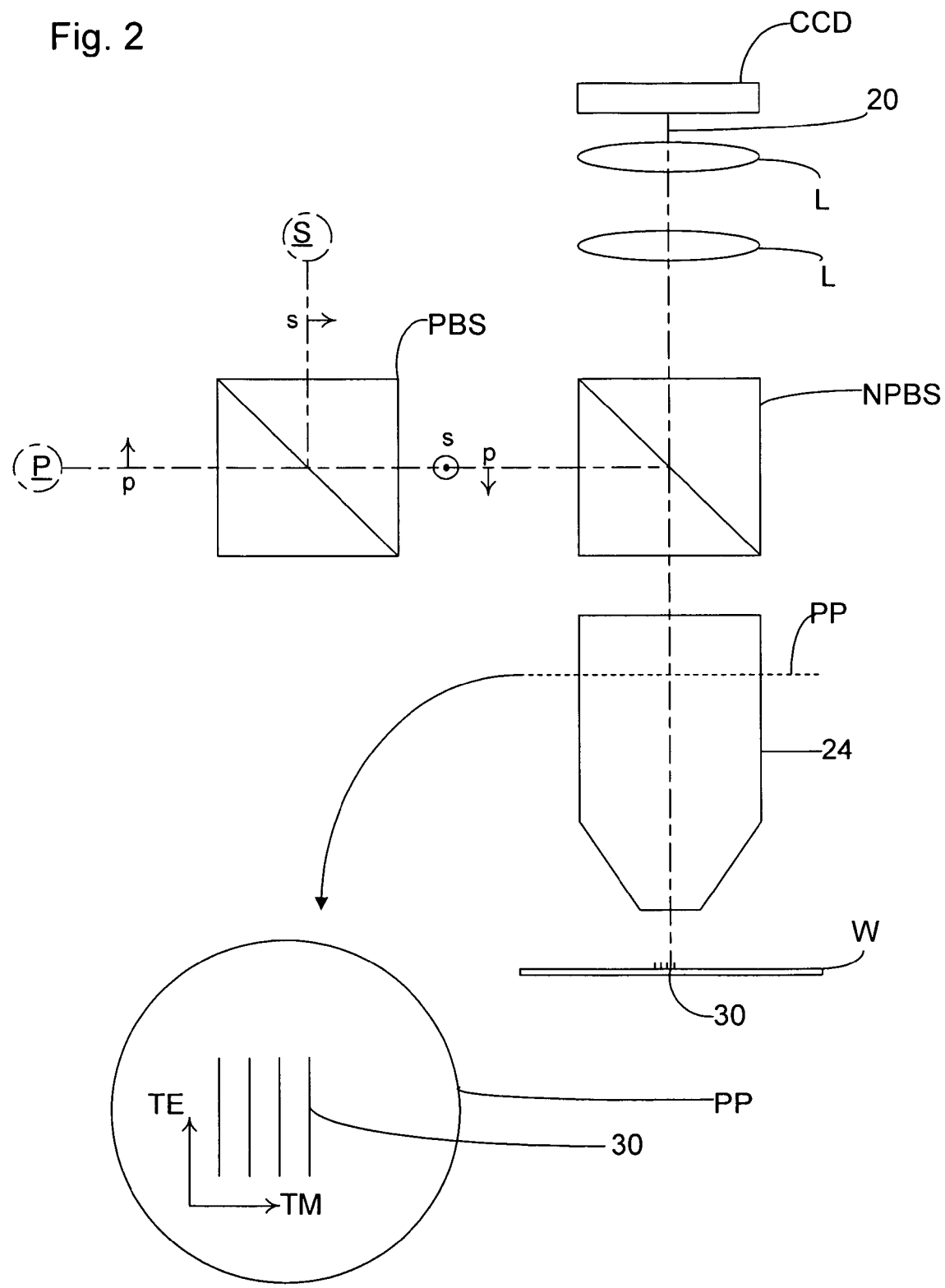
FIG. 2 depicts an inspection apparatus according to the state of the art.

At this point 20, the beam is known as either a TM (transverse magnetic) polarized beam or a TE (transverse electric) polarized beam. Polarization in a p or TM direction is parallel to the plane of incidence and the magnetic (M) field is perpendicular to the place of incidence. An s beam or TE beam is perpendicular to the plane of incidence and the electric (E) field is parallel to the plane of incidence. The direction of polarization at the pupil plane PP is shown in FIG. 2. The plan view of pupil plane PP is shown in a circle with grating 30 in the center of the circle and the orthogonal polarization directions TE and TM being shown with respect to the grating.

Figure 3:
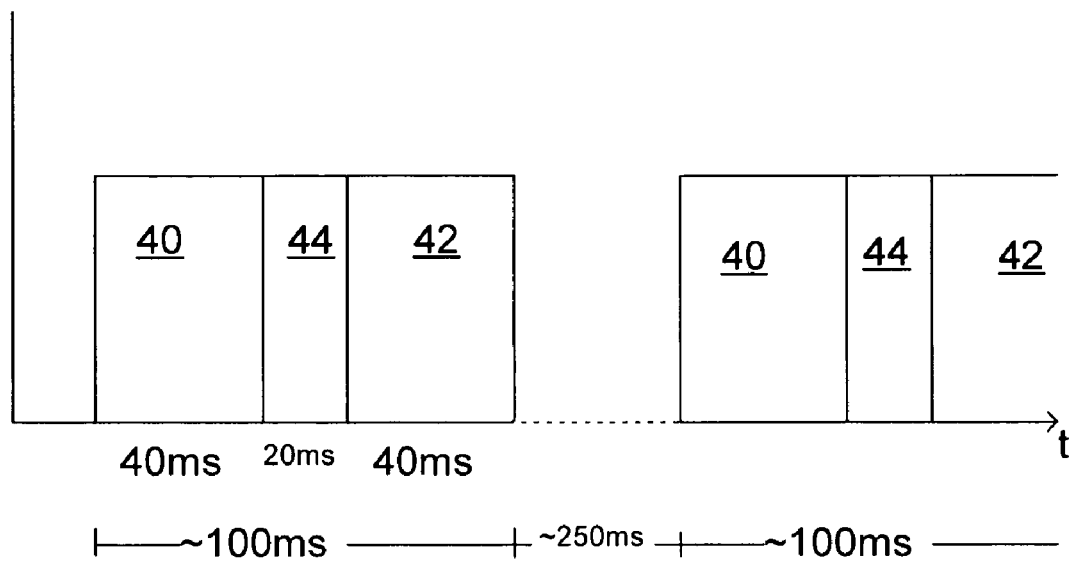
FIG. 3 depicts a time line according to FIG. 2.
Figure 4:
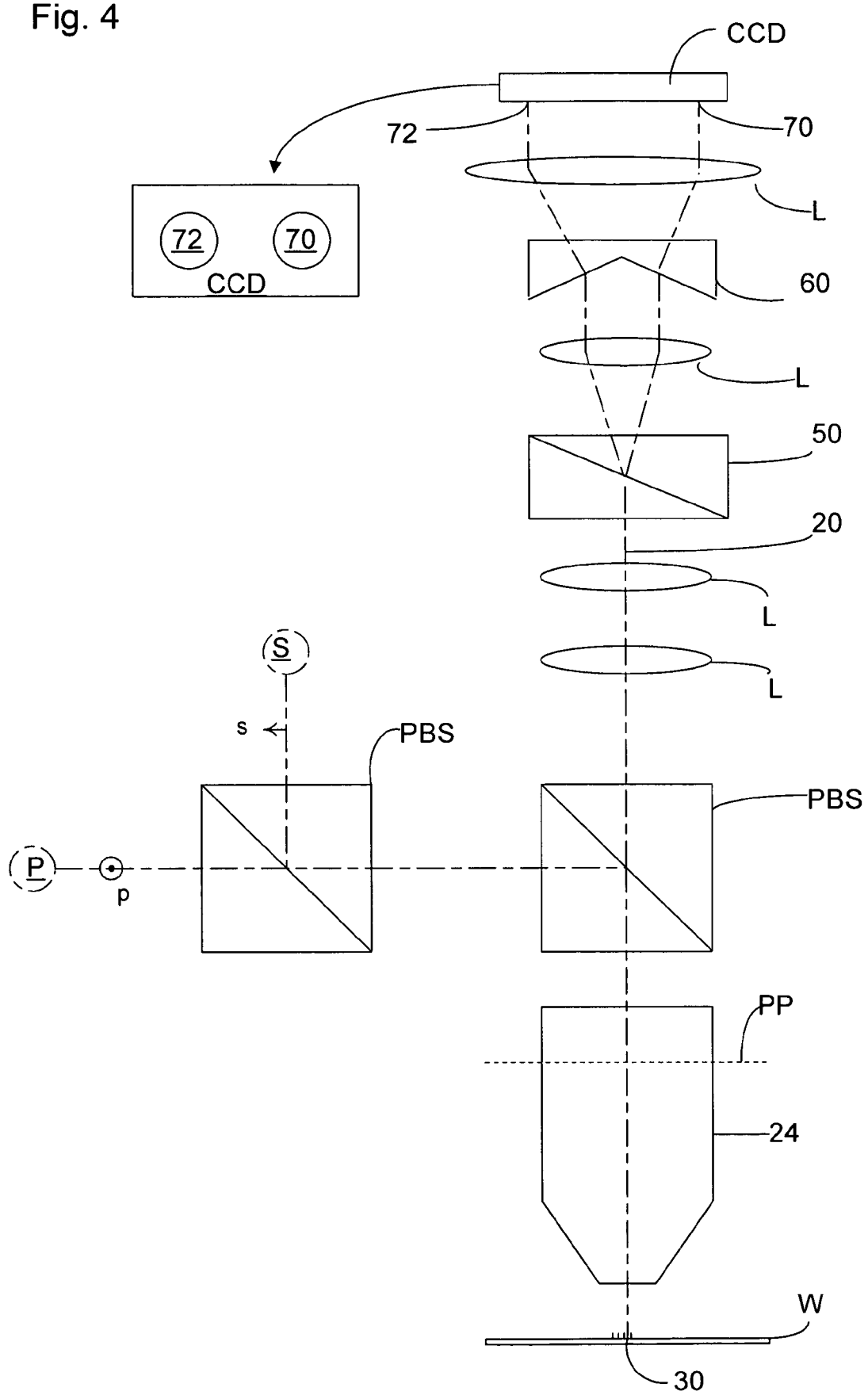
FIG. 4 depicts an inspection apparatus according to an embodiment of the invention.

FIG. 3 shows a timeline of the process of detecting both the TE and TM polarization directions. The TE acquisition 40 takes approximately 40 ms. The process 44 of opening and closing respective shutters takes approximately 20 ms. The subsequent TM acquisition 42 takes another 40 ms. The total time taken to measure the diffracted spectrum is therefore approximately 100 ms. Putting a different grating or a different substrate under the microscope objective 24 takes in the region of 250 ms. A first shutter is closed and TE acquisition 40 for the next substrate grating takes place again, taking another 40 ms, and so on. The mechanical movement of the substrate takes a finite amount of time (250 ms in this case) and is difficult to shorten. The aim of the present invention, therefore, is to shorten the diffracted spectrum acquisition time from 100 ms. FIG. 4 shows the inspection apparatus used to shorten this time.

Figure 5:
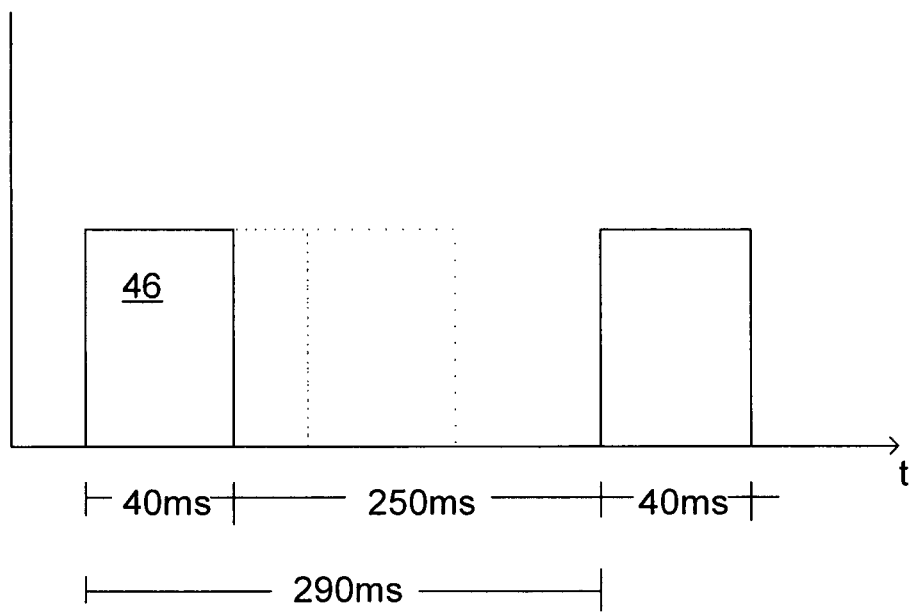
FIG. 5 depicts a time line according to FIG. 4.

What the inspection apparatus of FIG. 4 is able to do that known systems are not able to do is to allow the camera CCD to acquire both the TM and TE polarization spectrums at the same time. This cuts out the need for the shutters (and therefore eliminates the shutter opening and closing time) and shortens the time of acquisition of both TM and TE spectra to 40 ms for both as shown in FIG. 5. The total time taken to acquire the spectra and change the grating is reduced from 350 ms in FIG. 3 to approximately 290 ms in FIG. 5.

The way this is done is that the shutters are removed from the radiation sources P, S as shown in FIG. 4. Both these s and p polarized radiation beams are passed through a polarizing beam splitter PBS and deflected to a non-polarizing beam splitter NPBS. The combined beams pass through the microscope objective 24 as in the prior art and are diffracted from the grating 30 on the substrate W, before being reflected back via the non-polarizing beam splitter NPBS. Upon passing through the two lenses L, the combined beams pass through a Wollaston prism 50 in the pupil plane of the lens system. The Wollaston prism is made of a birefringent material that is used as a polarizer. It is made of two materials, each material having a "fast direction" and a "slow direction" such that a beam that is polarized in one direction will move more quickly through one of the materials than a beam polarized in the orthogonal direction. As the s-beam passes from the first material to the second material, it is effectively "bent" to the right because it suddenly gains speed upon reaching the boundary between the two materials. The p-beam, which is polarized in the orthogonal direction, does the opposite, i.e. it slows down as it reaches the boundary between the two materials, and is therefore bent in the opposite direction. The two beams independently (but simultaneously) pass through another focusing lens L before passing through an optical wedge 60. The optical wedge function can be realized in other ways, such as by using tilted mirrors with different tilt angles, as long as the optical wedge 60 redirects the light in different directions, allowing the measurement of multiple beams in parallel. The optical wedge is placed in the image plane of the system. The two separated orthogonally polarized radiation beams then pass through a further focusing lens (system) L before impinging on the CCD camera at positions 70 and 72, which are the s-spectrum and p-spectrum respectively. In this way, image acquisition can be measured simultaneously, cutting by more than half the image acquisition time (as shown in FIG. 5 and described above).

Figure 6:
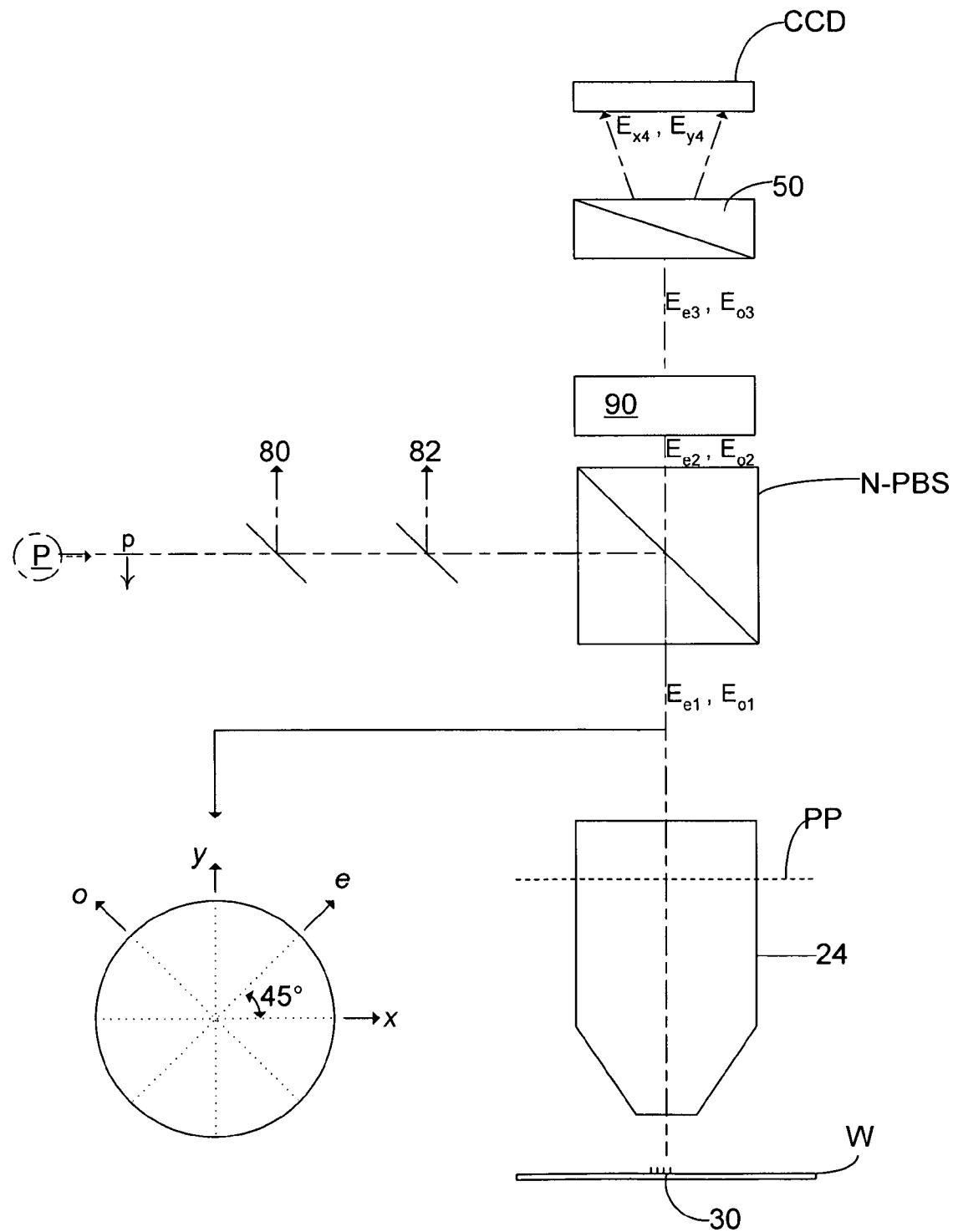
FIG. 6 depicts an ellipsometer according to the state of the art.

The second embodiment of the present invention enables more parameters of the orthogonally polarized beams to be measured. FIG. 6 shows an example of an ellipsometric sensor (or an ellipsometer) based on the prior art. Ellipsometry is the measurement of the state of polarization of scattered light. Ellipsometry measures two parameters; the phase difference ($\Delta$) between two differently polarized beams and an amplitude ratio (tan $\Psi$) of two polarized beams. With these two parameters, any polarization state of a purely polarized beam may be described. Specifically, if an incident beam has both s and p polarizations, the reflected beam will have reflectance coefficients $R_p$ and $R_s$. The complex amplitudes of each polarization direction are represented by $E_p$ and $E_s$ and are calculated as $R_p.p$ and $R_s.s$, respectively. $\Delta$ is the phase difference between $E_p$ and $E_s$ and tan $\Psi$ is the ratio of $E_p$ to $E_s$. In other words, $$\Delta = \arg(E_p - E_s) \quad (1)$$

$$\tan \Psi = E_p/E_s \quad (2)$$

Figure 7:
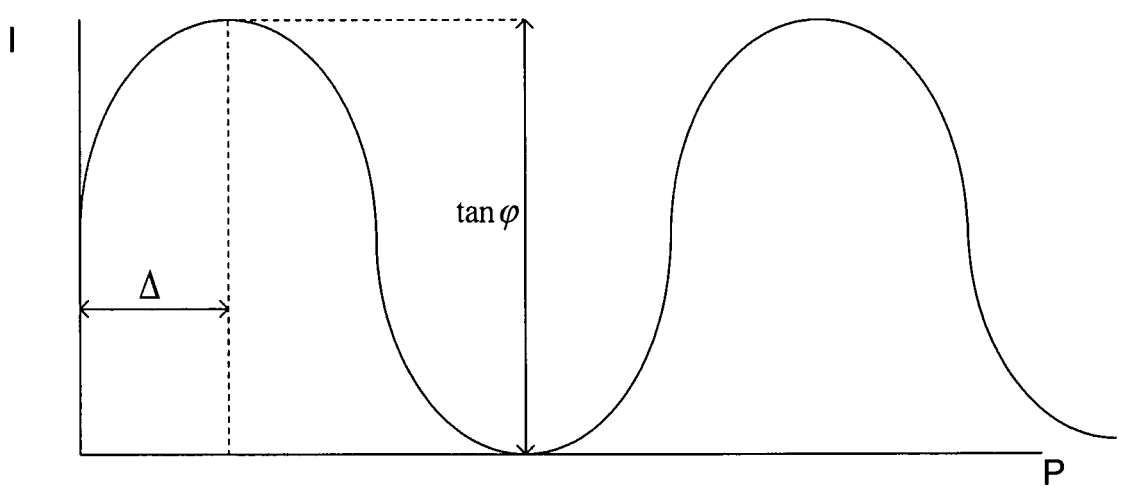
FIG. 7 depicts the properties of a radiation beam as found by an ellipsometer.

FIG. 7 shows the relationship between these two parameters. In particular, it shows the intensity variation in one pixel as a function of phase difference between S and P that is imposed by the phase modulator. In the example shown, intensity is completely modulated an so the amplitudes of $E_s$ and $E_p$ must be equal. As shown in FIG. 7, I is the intensity of the beam and P is the overall polarization of $E_p$ and $E_s$. If the two amplitudes are the same (i.e. $E_p = E_s$), the intensity of the overall beam is at a minimum because the orthogonal wave directions cancel each other out.

FIG. 6 shows illumination radiation from source P that is linearly polarized along one of the two eigen-polarizations of the three beam splitters that are present in the sensor (i.e. in the x or y direction as shown in FIG. 6). This ensures that the pupil plane is illuminated with the well-defined linear polarization state regardless of the polarization dependencies of the beam splitters. The three beam splitters 80, which sends part of the illumination to an imaging branch, 82, which sends part of the illumination to a focus branch and N-PBS, which is a non-polarizing beam splitter.

FIG. 6 also shows an eo-coordinate system that is oriented along the extraordinary and ordinary axes of a phase modulator 90. This phase modulator can, for example, be an electro-optic modulator (Pockels cell) or a mechanically adjustable modulator (Berek's compensator or Soleil-Babinet). (Refer to Hecht Zajac; "Optics" (Addison Wesley) for information on Soleil-Babinet modulators.) This coordinate system is rotated 45° relative to the xy-coordinate system.

The sensor is analyzed using a Jones matrix formulation with the eo-coordinate system as a basis. Note that the sensor may alternatively be analyzed with a Mueller matrix representation to take depolarization effects of optical components into account. The scattered beam in the pupil plane is given by a Jones vector $$\vec{J}_S = \begin{bmatrix} E_{e1} \\ E_{o1} \end{bmatrix} \quad (3)$$

Here $E_{o1}$ and $E_{e1}$ are the unknown complex amplitudes of the scattered fields along, respectively, the e and o directions. These amplitudes are determined by the object 30 (e.g. the grating, thin film or similar on the substrate) under investigation and the polarization dependency of the high-NA microscope objective 24. The Jones vector of the field that is transmitted by the non-polarizing beam splitter N-PBS is $$\begin{bmatrix} E_{e2} \\ E_{o2} \end{bmatrix} = \frac{1}{2} \begin{bmatrix} T_P + T_S & -T_P + T_S \\ -T_P + T_S & T_P + T_S \end{bmatrix} \begin{bmatrix} E_{e1} \\ E_{o1} \end{bmatrix} \quad (4)$$

where T is the transmission coefficient of the polarized beams.

This field is then sent through the phase modulator 90 that introduces a known phase shift $\phi$ between the e and o components of the polarized beam. As a result, the Jones vector of the field that is transmitted by the phase modulator 90 is $$\begin{bmatrix} E_{e3} \\ E_{o3} \end{bmatrix} = \frac{1}{2} \begin{bmatrix} e^{j\varphi} & 0 \\ 0 & 1 \end{bmatrix} \begin{bmatrix} T_P + T_S & -T_P + T_S \\ -T_P + T_S & T_P + T_S \end{bmatrix} \begin{bmatrix} E_{e1} \\ E_{o1} \end{bmatrix} \quad (5)$$

Finally, the light is transmitted by the Wollaston prism 50 that spatially separates the incoming beam into two beams that are orthogonally and linearly polarized along the x and y directions. These spatially separated fields that are incident on a CCD camera are given by $$\begin{bmatrix} E_{x4} \\ E_{y4} \end{bmatrix} = \frac{1}{4}\sqrt{2} \begin{bmatrix} 1 & -1 \\ 1 & 1 \end{bmatrix} \begin{bmatrix} e^{j\varphi}(T_P + T_S) & e^{j\varphi}(-T_P + T_S) \\ -T_P + T_S & T_P + T_S \end{bmatrix} \begin{bmatrix} E_{e1} \\ E_{o1} \end{bmatrix} \quad (6)$$

$$= \frac{1}{4}\sqrt{2} \begin{bmatrix} e^{j\varphi}(T_P + T_S) - (T_S - T_P) & e^{j\varphi}(-T_P + T_S)(T_P + T_S) \\ e^{j\varphi}(T_P + T_S) + (T_S - T_P) & e^{j\varphi}(-T_P + T_S) + (T_P + T_S) \end{bmatrix}$$
$$\begin{bmatrix} E_{e1} \\ E_{o1} \end{bmatrix}$$

If the beam splitter were perfectly non-polarizing in transmission, we would have $$T_p = T_s = T \quad (7)$$

In that case, the spatially separated fields $E_{x4}$ and $E_{y4}$ that are incident on the CCD are given by:

$$\begin{bmatrix} E_{x4} \\ E_{y4} \end{bmatrix} = \frac{1}{2}\sqrt{2} \begin{bmatrix} e^{j\varphi}T & -T \\ e^{j\varphi}T & T \end{bmatrix} \begin{bmatrix} E_{e1} \\ E_{o1} \end{bmatrix} \quad (8)$$

The intensities I of the two spatially separated beams on the CCD are then simply:

$$I_{x4} = \frac{1}{2}|T|^2[|E_{e1}|^2 + |E_{o1}|^2 - 2|E_{e1}||E_{o1}|\cos(\varphi + \Delta)] \quad (9)$$

$$I_{y4} = \frac{1}{2}|T|^2[|E_{e1}|^2 + |E_{o1}|^2 + 2|E_{e1}||E_{o1}|\cos(\varphi + \Delta)]$$

FIG. 7 shows the relationship of intensity I against overall polarization P ($E_p$ and $E_s$) of the polarized beams. If $E_p$ and $E_s$ are the same, intensity I reaches an inflexion for $\Psi = -\Delta$.

As derived from FIG. 7, $\Delta$ is the phase difference between, say, $E_{e1}$ and $E_{o1}$ that can easily and accurately be measured by measuring the intensities for various known phase steps $\phi$. This procedure is analogous to phase-stepped interferometry.

The three ellipsometric quantities $\tan(\Psi) = |E_{e1}|/|E_{o1}|$, $\cos(\Delta)$ and $\sin(\Delta)$ can be derived from $I_{x4}$ (or alternatively from $I_{y4}$) as follows:

The intensities $I_{x4}$ and $I_{y4}$ are measured for a series of different phase steps $\phi_i$. The number N of phase steps is at least three but more phase steps are desirable since this increases the measurement accuracy. The phase steps are distributed over a range of $2\pi$ radians. Often the phase steps are evenly distributed but this is not necessary.

In this manner, N intensities $I_{x4,i}$ and $I_{y4,i}$ for $i \in 1 \ldots N$ are measured. A harmonic curve given by:

$$I_{x4} = |E_{e1}|^2 + |E_{o1}|^2 - 2|E_{e1}||E_{o1}|\cos(\phi + \Delta)$$

$$I_{y4} = |E_{e1}|^2 + |E_{o1}|^2 + 2|E_{e1}||E_{o1}|\cos(\phi + \Delta) \quad (10)$$

is fitted through the measured intensities using standard least-square fitting techniques. The transmission T is set to unity. The analysis that will follow now shows that the results are independent of the actual value of T.

The maxima and minima of these harmonic curves are easily found and are denoted by $I_{x4,MAX}$, $I_{x4,MIN}$ and $I_{y4,MAX}$, $I_{y4,MIN}$ for $I_{x4}$ and $I_{y4}$, respectively. These extremes can be written as:

$$I_{x4,MAX} = (|E_{e1}| + |E_{o1}|)^2$$

$$I_{x4,MIN} = (|E_{e1}| - |E_{o1}|)^2 \quad (11)$$

It is only possible to show the extremes for $I_{x4}$ since it can be easily verified that $I_{y4}$ has the same extremes. We can also write:

$$\sqrt{I_{x4,MAX}} = |E_{e1}| + |E_{o1}|$$

$$\sqrt{I_{x4,MIN}} = |E_{e1}| - |E_{o1}| \quad (12)$$

This can be re-arranged to give:

$$2|E_{e1}| = \sqrt{I_{x4,MAX}} + \sqrt{I_{x4,MIN}}$$

$$2|E_{o1}| = \sqrt{I_{x4,MAX}} - \sqrt{I_{x4,MIN}} \quad (13)$$

Taking the ratio between these expressions gives:

$$\tan(\psi) = \frac{|E_{e1}|}{|E_{o1}|} = \frac{\sqrt{I_{x4,MAX}} + \sqrt{I_{x4,MIN}}}{\sqrt{I_{x4,MAX}} - \sqrt{I_{x4,MIN}}} \quad (14)$$

The other two remaining quantities $\cos(\Delta)$ and $\sin(\Delta)$ are determined by calculating:

$$C = \frac{1}{2\pi} \int_0^{2\pi} I_{x4} \cos(\varphi) d\varphi \quad (15)$$
$$= 2|E_{e1}||E_{o1}|\cos(\Delta)$$

$$S = \frac{1}{2\pi} \int_0^{2\pi} I_{x4} \sin(\varphi) d\varphi$$
$$= 2|E_{e1}||E_{o1}|\sin(\Delta)$$

Taking the ratio of S and C yields:

$$\Delta = a\tan\left(\frac{S}{C}\right) \quad (16)$$

The signs of C and S can be used to determine the correct quadrant in which $\Delta$ is located.

A problem with the prior art as shown in FIG. 6 is that beamsplitters that are truly non-polarizing in transmission are very hard, if not impossible, to realize. This is due to the fact that the s and p components of the fields that are transmitted by the beamsplitter generally experience different amplitude and phase changes upon transmission through the tilted splitting surface. This difference between the complex transmittances $T_P$ and $T_S$ results in error terms that reduce the sensitivity and that introduce substantial errors in the measurement of $\Delta$. This problem has been very difficult to solve: a number of solutions could be envisioned that are not considered to be practical:

1. Calibration of this error is extremely complicated due to the fact that it is interleaved with polarization effects in the objective. These errors can be corrected for on the assumption that the beamsplitter is sufficiently perfect in transmission. As soon as the beamsplitter introduces significant polarization errors, however, separating beamsplitter and objective polarization effects becomes extremely complex.

2. Reducing the split angle of the beam splitter reduces this error but results in long and unpractical optical tracklengths that complicate the realization of a compact sensor in a small volume.

3. One could equalize the complex transmission of the s and p polarizations with a stack of materials. The beamsplitter plane is built up of a multilayer thin film stack with such a composition that the transmission through this stack is polarization insensitive. The complex transmission may thereby be equalized. However, this can only be achieved over a small wavelength interval, which makes an extension to broadband angle-resolved micro-ellipsometry impossible. The term micro-ellipsometry is used to refer to the measurement concept in which a very high numerical aperture lens is used to make a small measurement spot. This allows localized ellipsometry with a spatial resolution in the micrometer region. The desirability of this is that it is a method that can collect a great amount of information, for example, it can measure the refractive index of a thin film for various wavelengths.

4. A pure metal beamsplitter could be used that has minimal depolarization effects. However, it has significantly more absorption than hybrid (e.g. dielectric) beamsplitters.

Figure 8:
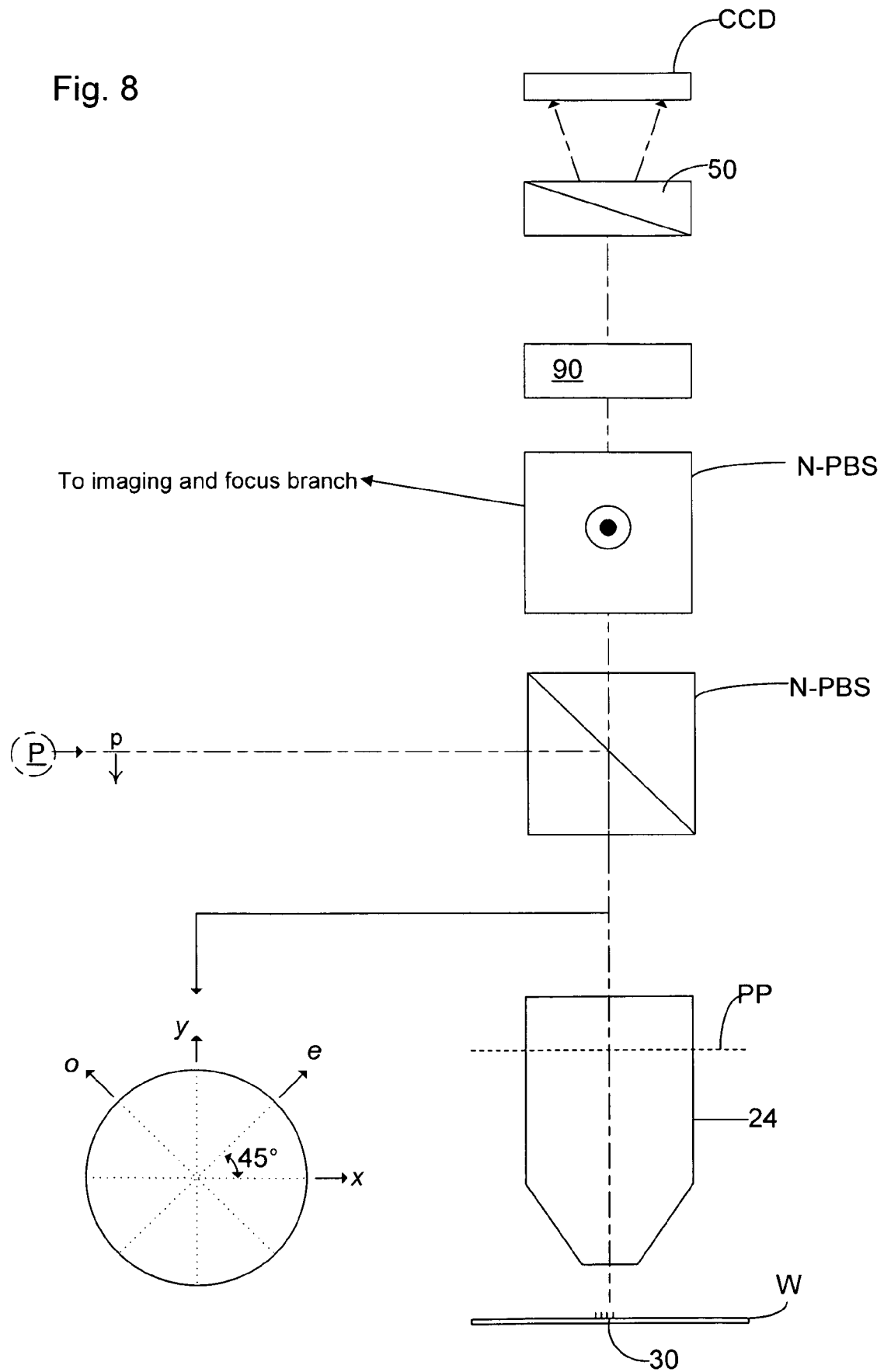
FIG. 8 depicts an ellipsometer according to an embodiment of the invention.
Figure 9:
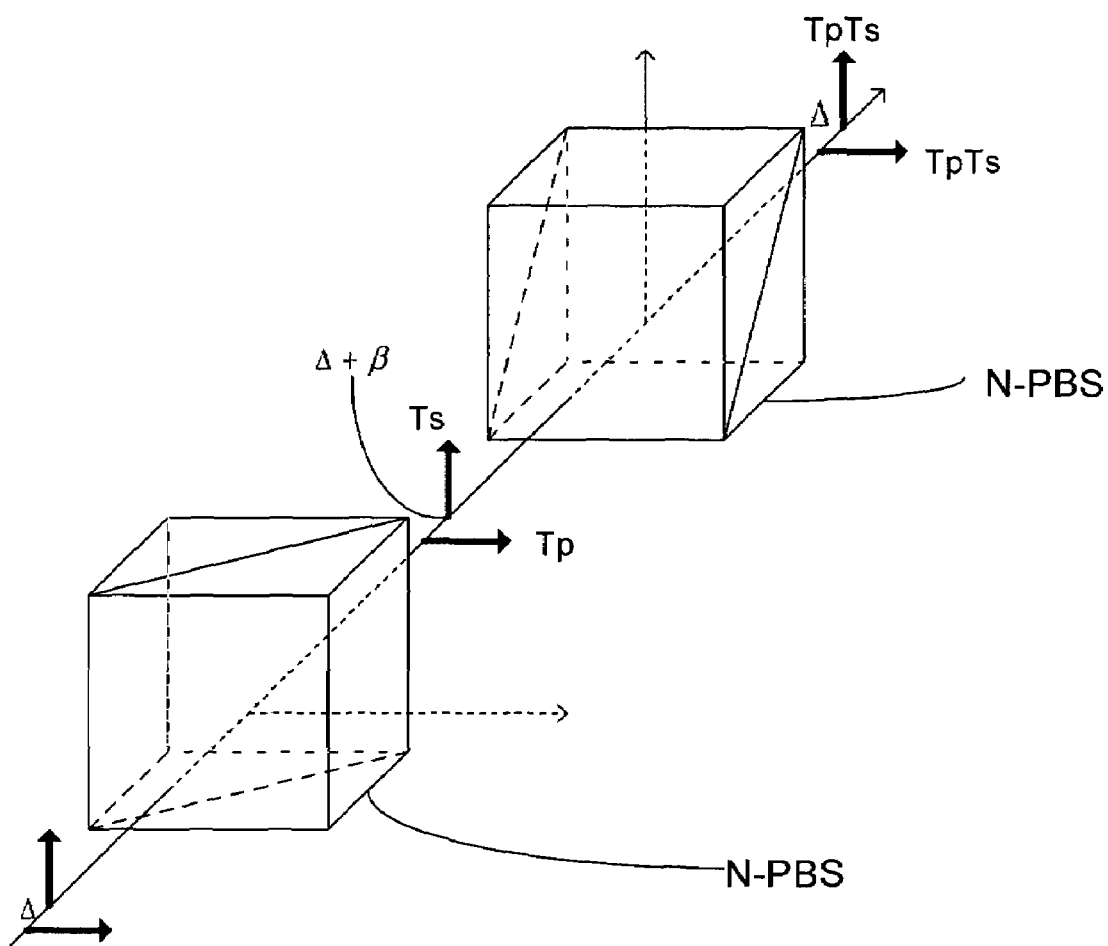
FIG. 9 depicts a portion of the embodiment of the invention of FIG. 8.

The invention that is proposed overcomes all of the limitations of the above-mentioned alternatives without complicating the existing system to any great extent. As shown in FIG. 8, a beamsplitter that is perfectly non-polarizing in transmission can be easily realized with two nominally identical non-polarizing beamsplitters N-PBS that are rotated 90° relative to each other, the two beamsplitters being shown in FIG. 9. As the beam that has been diffracted from the substrate grating passes through the first beamsplitter, the S and P components of the incident beam experience a different complex transmission by the beamsplitter. The second beamsplitter is rotated over 90° around the beam axis, which effectively interchanges S and P. As a result, the polarization change that has occurred in the first beamsplitter is undone by the second beamsplitter. The net result is that the polarization state of the input beam remains unchanged after transmission through the two beamsplitters.

Tracing the transmitted beam through these beamsplitters immediately shows the principle of this idea. Any phase shift $\beta$ that is introduced in the first beamsplitter is compensated for by the second beamsplitter. This is due to the fact that a beam that is p-polarized at the first beamsplitter becomes s-polarized at the second beamsplitter and vice versa. As a result, the net transmission of x and y components of the incident field is nominally equal.

Figure 10:
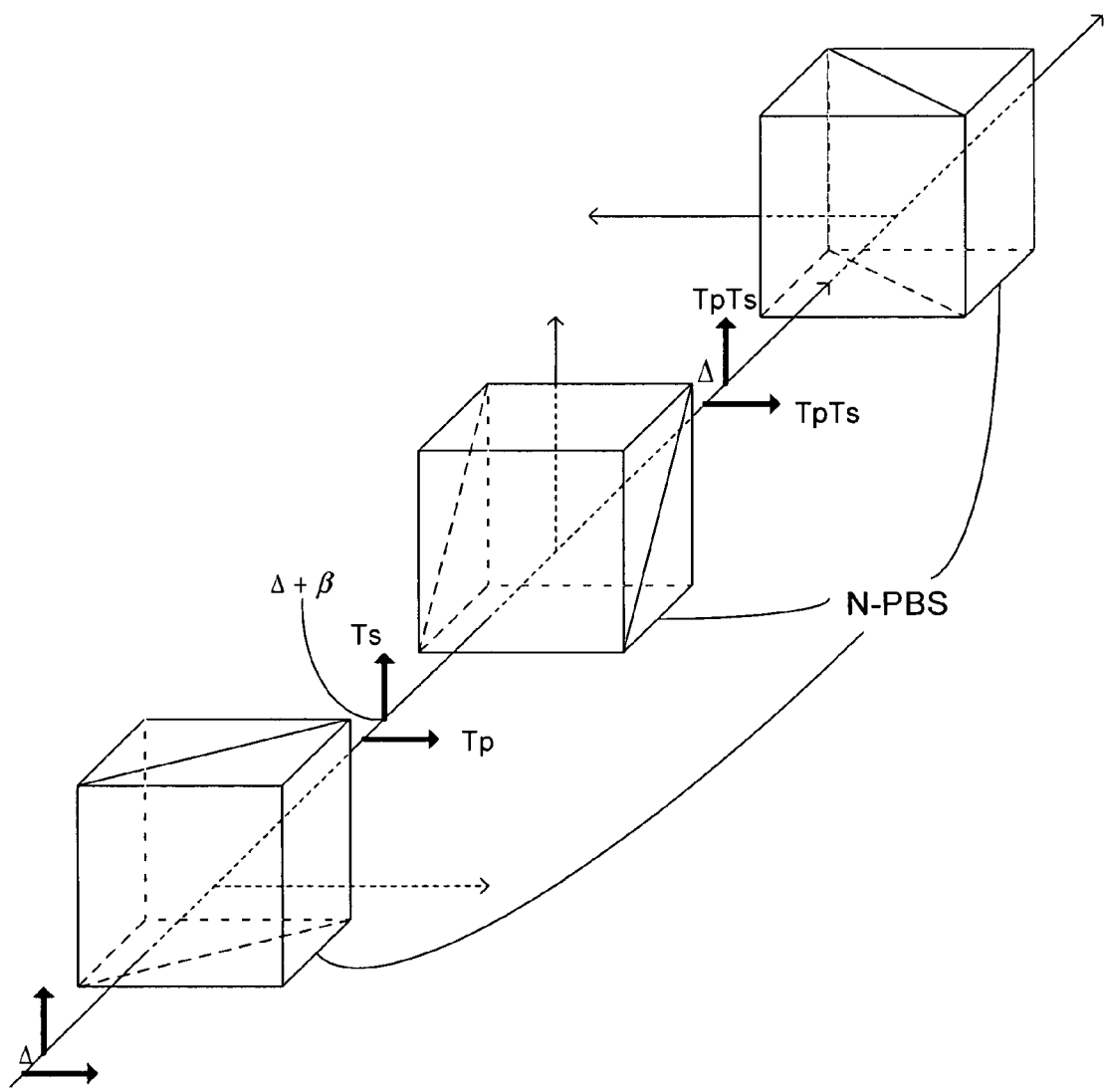
FIG. 10 depicts another embodiment of the invention.

The idea above is applied to a system with a phase modulator 90 in the measurement branch. However, this idea can also be realized with a phase modulator in the illumination branch. In that case, the idea of two beam splitters can be easily extended to a beam splitter that is truly non-polarizing in reflection. If necessary, one could add a third beamsplitter and make a composite beam splitter that is truly non-polarizing in reflection and transmission. This is shown in FIG. 10. A third non-polarising beamsplitter is inserted at the end of the illumination branch, that is again rotated by 90° with respect to the second beamsplitter, and so faces the opposite way relative to the first beamsplitter.

If the phase shifter 90 (with its modulation axis only the e-axis) is removed or turned to zero (i.e. with no phase shift), the apparatus of the first embodiment of this invention is effectively created. In other words, this ellipsometer acts as the inspection apparatus of FIG. 4 if there is no phase shift.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. It should be appreciated that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. An inspection apparatus configured to measure a property of a substrate, comprising:
 a light source configured to supply a radiation beam with two orthogonal polarized directions;
 a lens configured to focus the radiation beam with two orthogonal polarized directions onto a substrate;
 a beamsplitter configured to separate the radiation beam with two orthogonal polarized directions after it is reflected from a surface of the substrate into two orthogonally polarized sub-beams; and
 a detector system configured to detect simultaneously an angle-resolved spectrum of both orthogonally polarized sub-beams.

2. An inspection apparatus according to claim 1, further comprising an optical wedge configured to deflect the sub-beams further apart.

3. An inspection apparatus according to claim 1, wherein the beamsplitter comprises a polarizing prism.

4. An inspection apparatus according to claim 1, wherein the beamsplitter comprises a Wollaston prism.

5. An inspection apparatus according to claim 1, wherein the sub-beams comprise a TE-beam and a TM-beam.

6. An inspection apparatus according to claim 1, wherein the detector system is configured to detect both sub-beams in approximately 40 ms.

7. An inspection apparatus according to claim 1, wherein the light source comprises at least a third polarization direction.

8. A method of measuring a property of a substrate, comprising:
- providing a radiation beam with orthogonal polarization directions;
- reflecting the radiation beam off a surface of a substrate;
- splitting the reflected radiation beam into its respective orthogonally polarized sub-beams; and
- simultaneously detecting both sub-beams.

9. An inspection apparatus configured to measure a property of a substrate, comprising:
- a light source configured to supply a radiation beam with two orthogonal polarization directions;
- a lens configured to focus the radiation beam onto a substrate;
- a detector system configured to detect the radiation beam reflected from the substrate;
- a first non-polarizing beamsplitter configured to receive the radiation beam from the source in a first direction and to reflect the radiation beam in a second direction onto the substrate and to receive the radiation beam reflected from the substrate in the second direction and to pass the radiation beam towards the detector system;
- a second non-polarizing beamsplitter rotated 90° with respect to the first non-polarizing beamsplitter and configured to receive the radiation beam passed from the first non-polarizing beamsplitter in the second direction, to transmit a portion of the radiation beam in the second direction to the detector, and to reflect another portion of the radiation beam in a third direction, wherein the third direction is perpendicular to the second direction; and
- a third polarizing beamsplitter configured to receive the radiation beam passed from the second non-polarizing beamsplitter, to separate the radiation beam into orthogonally polarized sub-beams, and to pass the sub-beams to the detector system, wherein
- the detector system is configured to detect simultaneously the reflection spectrum of both sub-beams.

10. An inspection apparatus according to claim 9, wherein the third beamsplitter is a Wollaston prism.

11. An inspection apparatus according to claim 9, further comprising a focusing system and an optical wedge placed in the image plane of the focusing system configured to redirect the orthogonally polarized sub-beams in different directions such that the sub-beams are received at different positions on the detector system.

12. An inspection apparatus according to claim 9, further comprising a focusing system and tilted reflectors placed in the image plane of the focusing system configured to redirect the orthogonally polarized sub-beams in different directions such that the sub-beams are received at different positions on the detector.

13. An inspection apparatus according to claim 9, further comprising a phase shifter configured to shift the phase of the radiation beam by a predetermined amount.

14. An inspection apparatus according to claim 13, wherein the phase shifter is configured to shift the phase of the radiation beam by 0°.

15. An inspection apparatus according to claim 13, wherein the phase shifter comprises a translating compensator.

16. An inspection apparatus according to claim 13, wherein the phase shifter comprises a tilting compensator.

17. An inspection apparatus according to claim 13, wherein the phase shifter comprises a non-linear crystal to which a voltage is applied to change the phase of radiation passing through the crystal.

18. An inspection apparatus according to claim 17, wherein the non-linear crystal is a Pockel's cell.

19. An inspection apparatus according to claim 9, further comprising a fourth non-polarizing beamsplitter configured to combine with the first and second non-polarizing beamsplitters to act as a composite beamsplitter.

20. An inspection apparatus according to claim 9, wherein the third direction is towards an imaging and focusing branch of the inspection apparatus.

21. A lithographic apparatus configured to measure a property of a substrate, comprising:
- a light source configured to supply radiation with two orthogonal polarization directions;
- a lens configured to focus the radiation beam with two orthogonal polarized directions onto a substrate;
- a beamsplitter configured to separate the radiation beam with two orthogonal polarized directions after it is reflected from a surface of the substrate into two orthogonally polarized sub-beams; and
- a detector system configured to detect simultaneously an angle-resolved spectrum of both orthogonally polarized sub-beams.

22. A lithographic apparatus configured to measure a property of a substrate, comprising:
- a light source configured to supply a radiation beam with two orthogonal polarization directions;
- a lens configured to focus the radiation beam onto a substrate;
- a detector system configured to detect the radiation beam reflected from the substrate;
- a first non-polarizing beamsplitter configured to receive the radiation beam from the source in a first direction and to reflect the radiation beam in a second direction onto the substrate and to receive the radiation beam reflected from the substrate in the second direction and to pass the radiation beam towards the detector system;
- a second non-polarizing beamsplitter rotated 90° with respect to the first non-polarizing beamsplitter and configured to receive the radiation beam passed from the first non-polarizing beamsplitter in the second direction, to transmit a portion of the radiation beam in the second direction to the detector and to reflect another portion of the radiation beam in a third direction, wherein the third direction is perpendicular to the second direction; and
- a third beamsplitter configured to receive the radiation beam passed from the second non-polarizing beamsplitter, to separate the radiation beam into orthogonally polarized sub-beams and to pass the sub-beams to the detector system, wherein
- the detector system is configured to detect simultaneously the reflection spectrum of both sub-beams.

23. A lithographic cell configured to measure a property of a substrate, comprising:
- a light source configured to supply radiation with two orthogonal polarization directions;
- a lens configured to focus the radiation beam onto a substrate;
- a beamsplitter configured to separate the radiation beam after it is reflected from a surface of the substrate into two orthogonally polarized sub-beams; and
- a detector system configured to detect simultaneously an angle-resolved spectrum of both orthogonally polarized sub-beams.

24. A lithographic cell configured to measure a property of a substrate, comprising:
- a light source configured to supply a radiation beam with two orthogonal polarization directions;
- a lens configured to focus the radiation beam onto a substrate;
- a detector system configured to detect the radiation beam reflected from the substrate;
- a first non-polarizing beamsplitter configured to receive the radiation beam from the source in a first direction and to reflect the radiation beam in a second direction onto the substrate and to receive the radiation beam reflected from the substrate in the second direction and to pass the radiation beam towards the detector system;
- a second non-polarizing beamsplitter rotated 90° with respect to the first non-polarizing beamsplitter and configured to receive the radiation beam passed from the first non-polarizing beamsplitter in the second direction, to transmit a portion of the radiation beam in the second direction to the detector and to reflect another portion of the radiation beam in a third direction, wherein the third direction is perpendicular to the second direction; and
- a third beamsplitter configured to receive the radiation beam passed from the second non-polarizing beamsplitter, to separate the radiation beam into orthogonally polarized sub-beams and to pass the sub-beams to the detector system, wherein the detector system is configured to detect simultaneously the reflection spectrum of both sub-beams.

* * * * *